United States Patent
Sun et al.

(10) Patent No.: US 8,295,907 B2
(45) Date of Patent: Oct. 23, 2012

(54) INTEGRATED FINITE ELEMENT AND CIRCULATORY MODEL FOR PREDICTING HEMODYNAMIC EFFECTS OF LEFT VENTRICULAR IMPAIRMENT, RESYNCHRONIZATION AND REMODELING

(75) Inventors: Ying Sun, Wakefield, RI (US); Frederick J. Vetter, South Kingston, RI (US); Rumei Dong, Kingston, RI (US); Salvatore A. Chiaramida, Charleston, SC (US)

(73) Assignee: Board of Governors for Higher Education, State of Rhode Island and Providence Plantations, Providence, RI (US)

( * ) Notice: Subject to any disclaimer, the term of this patent is extended or adjusted under 35 U.S.C. 154(b) by 767 days.

(21) Appl. No.: 11/778,231

(22) Filed: Jul. 16, 2007

(65) Prior Publication Data
US 2008/0004508 A1 Jan. 3, 2008

Related U.S. Application Data

(63) Continuation of application No. PCT/US2006/002382, filed on Jan. 23, 2006.

(60) Provisional application No. 60/645,807, filed on Jan. 21, 2005.

(51) Int. Cl.
*A61B 5/05* (2006.01)
(52) U.S. Cl. .................. 600/416; 382/128; 600/508
(58) Field of Classification Search .................. 600/407, 600/508, 509; 382/128
See application file for complete search history.

(56) References Cited

U.S. PATENT DOCUMENTS

| 6,295,464 | B1* | 9/2001 | Metaxas | 600/407 |
|---|---|---|---|---|
| 6,873,718 | B2 | 3/2005 | O'Donnell et al. | |
| 2002/0188170 | A1* | 12/2002 | Santamore et al. | 600/37 |
| 2003/0187362 | A1* | 10/2003 | Murphy et al. | 600/508 |
| 2004/0049115 | A1* | 3/2004 | Murphy et al. | 600/509 |
| 2004/0049116 | A1* | 3/2004 | Murphy et al. | 600/509 |
| 2004/0153128 | A1* | 8/2004 | Suresh et al. | 607/14 |
| 2004/0176678 | A1* | 9/2004 | Murphy et al. | 600/407 |
| 2004/0176679 | A1* | 9/2004 | Murphy et al. | 600/407 |
| 2005/0020929 | A1* | 1/2005 | Murphy et al. | 600/509 |
| 2005/0043609 | A1* | 2/2005 | Murphy et al. | 600/408 |
| 2005/0187461 | A1* | 8/2005 | Murphy et al. | 600/416 |

(Continued)

OTHER PUBLICATIONS

Watanabe et al. "Finite Element Analysis on the Relationship between Left Ventricular Pump function and fiber Structure within the Wall", JSME International Journal Series C vol. 46 (2003), No. 4 Special Issue on Bioengineering pp. 1330-1339.*

(Continued)

*Primary Examiner* — Carl H Layno
*Assistant Examiner* — Allen Porter, Jr.
(74) *Attorney, Agent, or Firm* — Gesmer Updegrove LLP

(57) ABSTRACT

A computational model which integrates a complex circulatory model and a finite element to determine the dynamics of a left ventricle continuously over consecutive cardiac cycles. The model includes determining a LV pressure ($p_{lv}$) using a circulatory model, using a finite element model $p_{lv}$ as input and determining a LV volume ($v_{lv}$), computing a LV elastance according to: $e_{lv}=p_{lv}/v_{lv}$, driving the circulatory model with the $e_{lv}$; and returning to determining a LV pressure and starting the next iteration, wherein the steps continue at a sufficient time resolution for a desired number of entire cardiac cycles. The dynamic Young's modulus functions are assigned to individual finite elements, resulting in a time-varying left ventricular elastance that drives the circulatory model.

20 Claims, 14 Drawing Sheets

U.S. PATENT DOCUMENTS

2006/0166176 A1* 7/2006 Lakin et al. .................. 434/262

OTHER PUBLICATIONS

Veress et al. "Physiologically realistic LV models to produce normal and pathological image and phantom data" Dept. of Bioeng., Utah Univ., Salt Lake City, UT; Nuclear Science Symposium Conference Record, 2004 IEEE Publication Date: Oct. 22, 2004 vol. 7, 4231-4235.*

Janz et al. "Finite-Element Model for the Mechanical Behavior of the Left Ventricle: Prediction of Deformation in the Potassium-Arrested Rat Heart" Circulation research, American Heart Association, 1972;30;244-252.*

Smith et al. "Analysis of Anatomic Structures Using Biquintic Finite Element Interpolation" Annals of Biomedical Engineering, Jun. 2000, vol. 28:6, p. 598-611.*

Hunter et al. "Modeling Total Heart Function" Annual Review of Biomedical Engineering; 2003 vol. 5 Issue 1, p. 147-180.*

Adamson et al., "Cardiac Resynchronization Therapy for Advanced Heart Failure", Current Treatment Options in Cardiovascular Medicine, 2003, pp. 301-309, vol. 5, Current Science Inc., US.

Bovendeerd et al., Regional wall mechanics in the ischemic left ventricle: numerical modeling and dog experiments:, American Journal of Physiology, 1996, pp. H398-H410, vol. 270, The American Physiological Society, US.

Chen et al. "The Surgical Treatment of Heart Failure. A New Frontier: Nontransplant Surgical Alternatives in Heart Failure", Cardiology in Review, 2002, pp. 326-333, vol. 10, No. 6, Lippincott Williams & Wilkins, US.

Guccione et al., "Mechanism underlying mechanical dysfunction in the border zone of left ventricular aneurysm: a finite element model study", The Annals of Thoracic Surgery, 2001, pp. 654-662, vol. 71, The Society of Thoracic Surgeons, Elsevier Science Inc., US.

Hunter et al., "Modeling Total Heart Function", Annu. Rev. Biomed. Eng., 2003, pp. 147-177, vol. 5, No. 1, Annual Reviews, US.

Ratcliffe et al., "The effect of ventricular volume reduction surgery in the dilated, poorly contractile left ventricled: A simple finite element analysis", The Journal of Thoracic and Cardiovascular Surgery, 1998, pp. 566-577, Vo. 116, American Association for Thoracic Surgery, US.

Sciagra et al. "Relationship of infarct size and severity versus left ventricular ejection fraction and volumes obtained from 99m Tc-sestamibi gated single-photon emission computed tomography in patients treated with primary percutaneous coronary intervention", European Journal of Nuclear Medicine and Molecular Imaging, Jul. 2004, pp. 969-974, vol. 31, Springer-Verlag.

Ying Sun, "Modeling the dynamic interaction between left ventricle and intra-aortic balloon pump", American Journal of Physiology, 1991, pp. H1300-H1311, the American Physiological Society, US.

Sun et al., "A comprehensive model for right-left heart interaction under the influence of pericardium and baroreflex", American Journal of Physiology, 1997, pp. H1499-H1515, the American Physiological Society, US.

Sun et al., "Estimation of intramyocardial pressure and coronary blood flow distribution", American Journal of Physiology, 1998, pp. H664-H672, the American Physiological Society, US.

Sun et al., "Mathematical model that characterizes transmitral and pulmonary venous flow velocity patterns", American Journal of Physiology, 1995, pp. H476-H489, the American Physiological Society, US.

Vetter et al., "Three-dimensional analysis of regional cardiac function: a model of rabbit ventricular anatomy", Progress in Biophysics & Molecular Biology, 1998, pp. 157-183, vol. 69, Elsevier Science Ltd.

Vetter et al., "Three-Dimensional Stress and Strain in Passive Rabbit Left Ventricle: A Model Study", Annals of Biomedical Engineering, 2000, pp. 781-792, vol. 28, Biomedical Engineering Society.

Vetter et al., "Mechanoelectric Feedback in a Model of the Passively Inflated Left Ventricle", Annals of Biomedical Engineering, 2000, pp. 414-426, vol. 29, Biomedical Engineering Society.

* cited by examiner

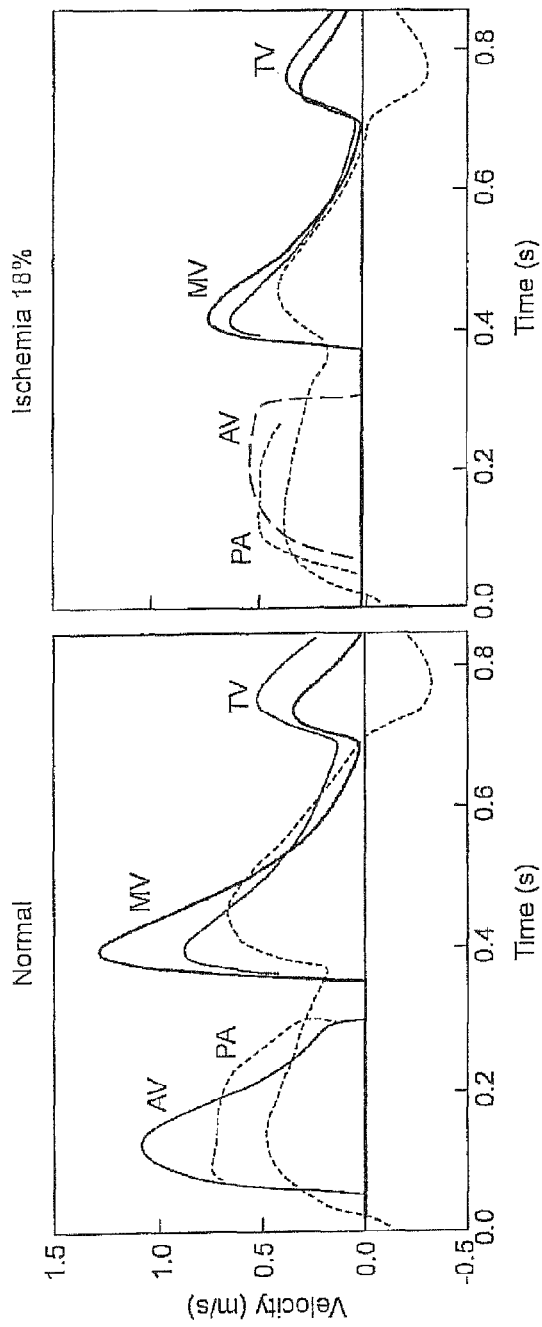
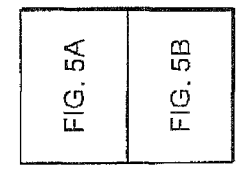
FIG. 4-3
FIG. 5 ent Cardio to an analog electrical model of the cardiovascular system. The

INTEGRATED FINITE ELEMENT AND CIRCULATORY MODEL FOR PREDICTING HEMODYNAMIC EFFECTS OF LEFT VENTRICULAR IMPAIRMENT, RESYNCHRONIZATION AND REMODELING

PRIORITY INFORMATION

This application is a continuation of International Application Serial No. PCT/US06/02382, filed on Jan. 23, 2006, which claims priority to U.S. Provisional Patent Application Ser. No. 60/645,807, filed on Jan. 21, 2005, all of which are incorporated herein by reference in their entirety.

BACKGROUND OF THE INVENTION

1. Field of the Invention

The present invention relates to a computational model capable of relating the left ventricular regional myocardial contraction to hemodynamics. The fields of use include cardiovascular and pharmaceutical research, computer assisted instruction in cardiovascular physiology, and planning for cardiac surgery and treatment procedures such as the ventricular restoration surgery Cohn L H. Chen F Y, Cohn L H. The surgical treatment of heart failure. A new frontier: non-transplant surgical alternatives in heart failure. Cardiology Review 10(6): 326-33, 2002. and the cardiac resynchronization therapy Adamson P B, Abraham W T. Cardiac resynchronization therapy for advanced heart failure. Current Treatment Options Cardiovascular Medicine 5(4): 301-309, 2003.

2. Description of the Prior Art

Finite element models are used to simulate behaviors of complex systems. There are many different models for a variety of different systems which are well known to those skilled in the art. Typically the systems are subdivided into interconnected elements that represent sections, in the material and react in such a way that they influence the reaction of their adjacent sections. The finite element model simulates this behavior by solving differential equations for each of the elements that represents a relatively small section in the material.

For the study of the mechanics of the myocardium of the left ventricle, several models based on finite element methods have been used in the past. Bovendeerd P H M, Arts T, Delhaas T, Huyghe J M, van Campen D H, Reneman R S. American Journal of Physiology 270: H398-H410, 1996 used a finite element model accounting for the thick-walled ventricular geometry to simulate the ischemic left ventricle during a complete cardiac cycle. Their model significantly over estimated (by about double) the loss of stroke work. Ratcliffe M B, Hong J, Salahieh A, Ruch S, Wallace A W. The effect of ventricular volume reduction surgery in the dilated, poorly contractile left ventricle: a simple finite element analysis. Journal of Thoracic Cardiovascular Surgery 116(4): 566-77, 1998 used a finite element analysis for the effect of ventricular volume reduction surgery. Their model predicted the left ventricular dynamics at end of systole and end of diastole, not for the entire cardiac cycle. Guccione J M, Moonly S M, Moustakidis P, Costa K D, Moulton M J, Ratcliffe M B, and Pasque M K. Mechanism underlying mechanical dysfunction in the border zone of left ventricular aneurysm: A finite element model study. Annals of Thoracic Surgery 71: 654-662, 2001 used a finite element model to characterize the mechanics of the border zone region of left ventricular aneurysm. Their model representation was also limited to the end-systolic and end-diastolic time instances. All the aforementioned models were focused on the left ventricle only and did not include a comprehensive representation of the circulatory system.

Sun Y, Beshara M., Lucariello R J, Chiaramida S A. A comprehensive model for right-left heart interaction under the influence of pericardium and baroreflex. American Journal of Physiology 272: H1499-H1515, 1997 developed a comprehensive analog electrical model to characterize the hemodynamics during heart failure and the right-left heart interaction under the influence of pericardium and baroreflex. While the analog circulatory model was capable of generating realistic and physiological pressure and flow waveforms at various parts of the cardiovascular system, it did not have a three-dimensional description of the left ventricular walls. Therefore, this model was incapable of relating regional impairment of left ventricular myocardium to its global effect on the hemodynamics of the entire cardiovascular system.

SUMMARY OF THE INVENTION

The combination of a finite element model of the left ventricular walls with a complex circulatory model so that one can predict the hemodynamic outcome of a regional left ventricular impairment.

This invention is directed to a computation model capable of relating the left ventricular regional myocardial contraction to hemodynamics. The model includes methods of integrating a finite element model of the left ventricle (LV) into an analog electrical model of the cardiovascular system. The resulting model is computationally efficient such that simulation of cardiovascular dynamics over several cardiac cycles can be obtain in a reasonable time frame. The computational model includes the use of time-varying Young's modulus of individual finite elements to define the global LV elastance over a cardiac cycle, the definition of infarct zone by reduced Young's modulus, the use of two or more 2D LV wall profiles to interpolate the 3D LV geometry, the interaction between the finite element model and the circulatory model via the LV elastance at every integration times step, the prediction of the hemodynamic effects of action potential propagation in the myocardium, and the use of the model to assess outcomes of LV infraction, cardiac, resynchronization therapy using biventricular pacing, and LV remodeling surgery. The model provides the basis for developing a commercial simulation software system that can be used by pharmaceutical and medical device industries, researches in cardiovascular dynamics, clinicians for diagnosis of congestive heart failure, educators and students for cardiovascular physiology.

BRIEF DESCRIPTION OF THE DRAWINGS

These and other features of the present invention will now be described in greater detail with reference to the accompanying drawings, wherein:

FIGS. 4 through 4-3 are hemodynamic waveforms generated by the model for normal and 18% infarction;

DETAILED DESCRIPTION OF THE INVENTION

Figure 1:
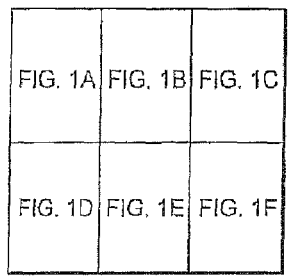
FIGS. 1 through 1F are a schematic diagram of the system showing the interaction between a finite element model of the left ventricle and an analog electrical model of the entire cardiovascular system.
Figure 1A:
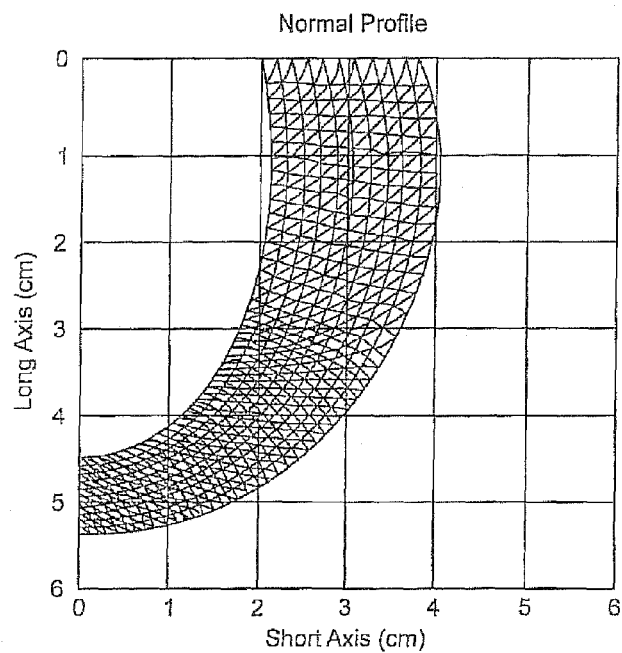
Figure 1A:
Figure 1B:
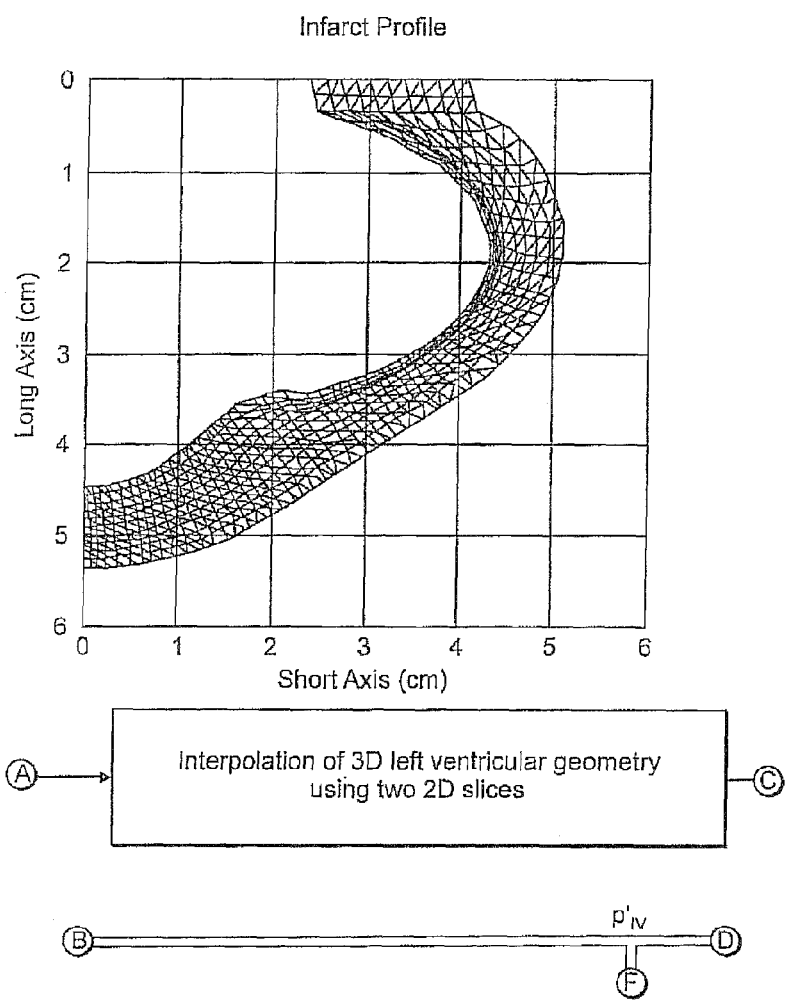
Figure 1C:
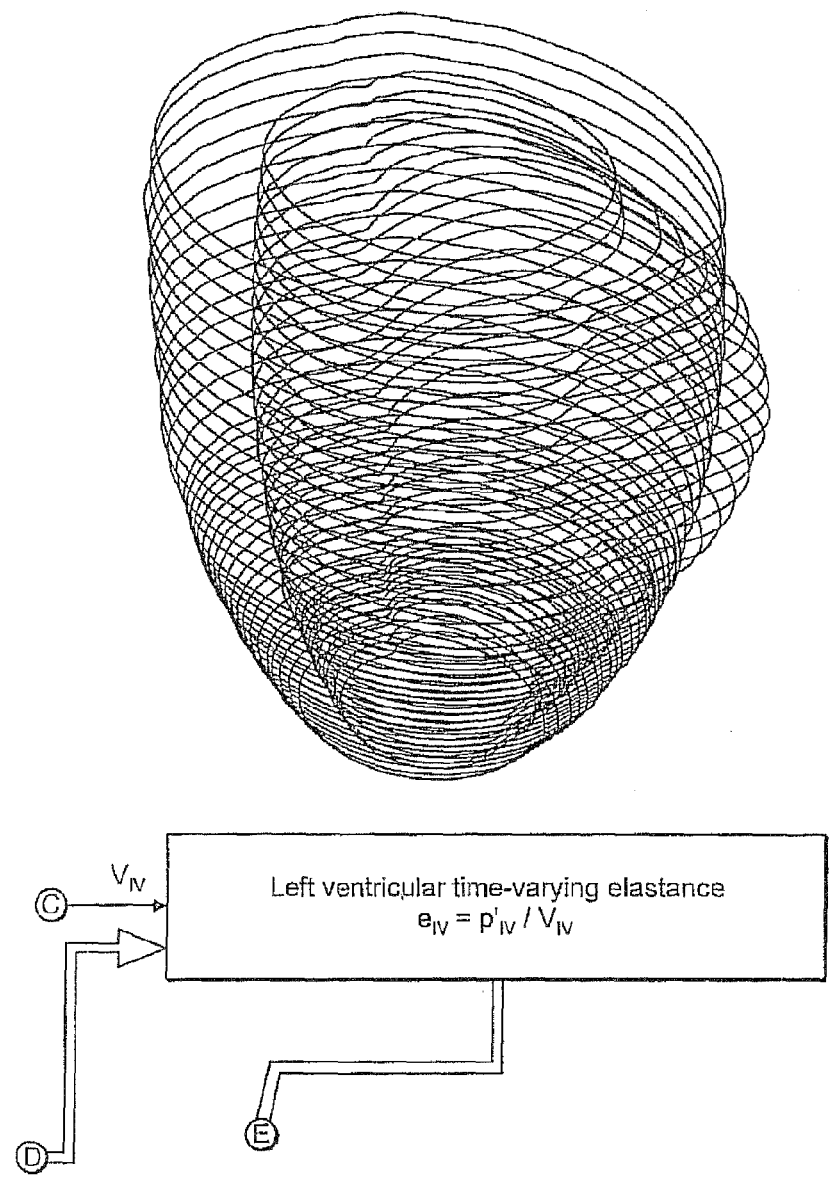
Figure 1D:
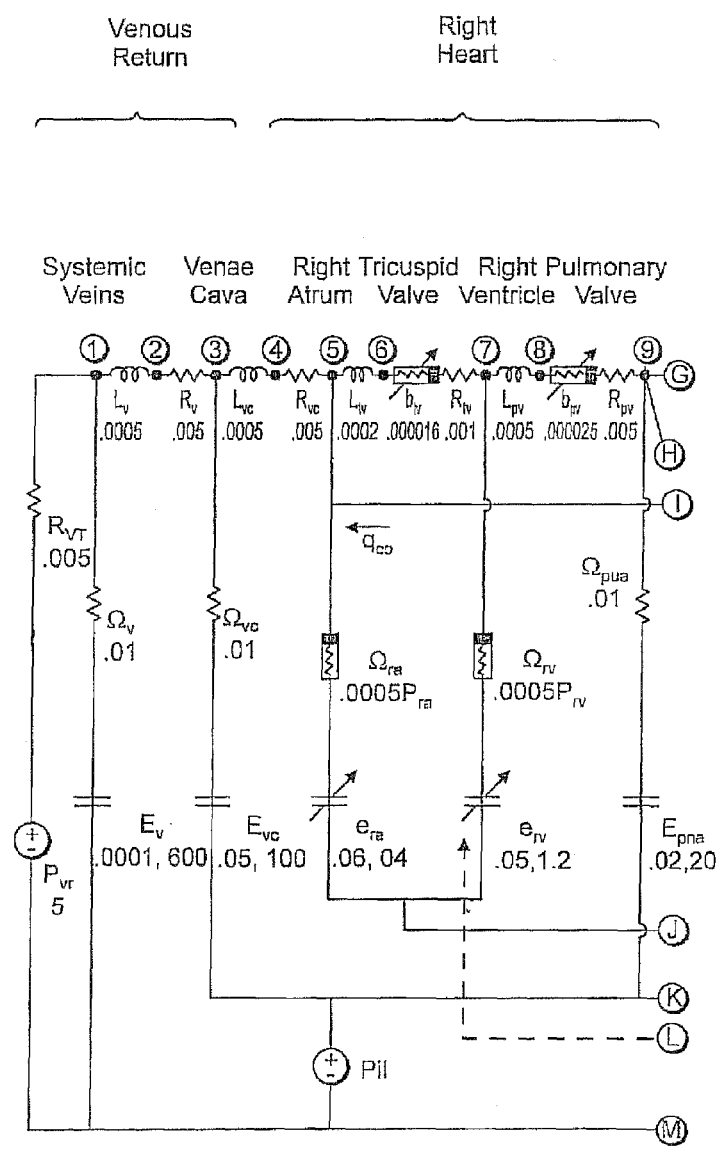
Figure 1E:
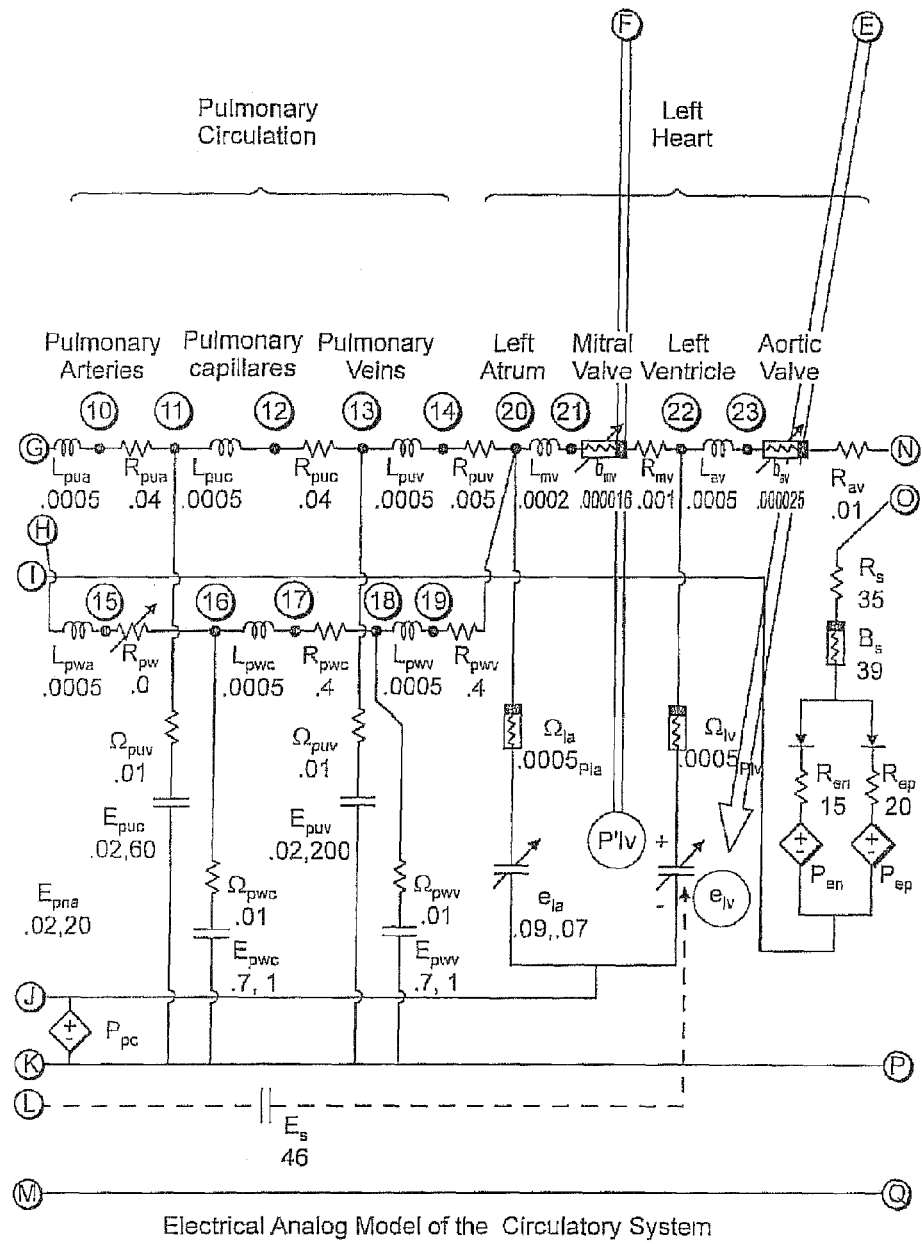
Figure 1F:
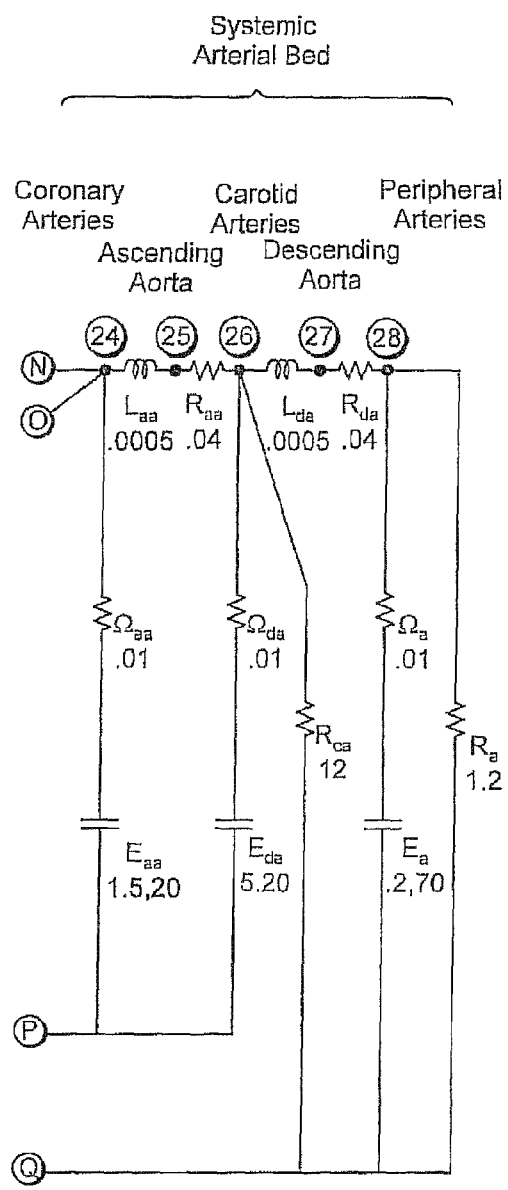

This invention integrates a complex circulatory model and a finite element dynamically and efficiently. It is presently the only available computational model that can relate LV regional myocardial contraction to the hemodynamic consequences for both transient and steady states of the cardiovascular dynamics. The 3-dimensional mesh generated by two 2-dimensional finite element calculations significantly decreases the computation time. Traditional 3D finite element LV models usually take days to compute and require supercomputers or clustered processors. With the algorithm, it is possible to run many cardiac cycles continuously to reveal the transient phase within a relative short time. The circulatory model is also much more comprehensive than the 3-element Windkessel model used in this type of models in the past. It includes the functions of four cardiac chambers, cardiac valves, pulmonary circulation, systemic arterial bed, and venous return. The model is physiological by generating realistic hemodynamic waveforms in response to changes of various physiological and/or pathophysiological variables. No other model is capable of representing these mechanisms in such a comprehensive way.

There are many advantages of the system including the use of time-varying Young's moduli of individual finite elements to define the global LV elastance over a cardiac cycle; the definition of infarct zone by reduced Young's modulus, the use of two or more 2D LV wall profiles to interpolate the 3D LV geometry, the interaction between the finite element model and the circulatory model via the LV elastance at every integration time step, the prediction of the hemodynamic effects of action potential propagation in the myocardium, and the use of the model to assess outcomes of LV infarction, cardiac resynchronization therapy using biventricular pacing, and ventricular restoration surgery.

The model provides a platform to describe normal and abnormal left ventricles, and predicts the hemodynamic consequences of a specific infarct zone. The model has several application areas including cardiovascular research, computer assisted instruction, pharmaceutical research, planning and assessment of LV remodeling surgery, optimization of cardiac resynchronization therapy by biventricular pacing, and relating medical imaging data (MRI, SPECT, echo) to diagnosis of congestive heart failure.

The model differs from present technology in that there is an integration of the finite element LV model and the circulatory model. This should bring the computation models out of pure research and find many applications in cardiology, cardiac surgery, medical device and pharmaceutical industry.

Thus, the model is a more sophisticated circulatory model and the representation of normal and infarct LV geometry. The computation efficiency is another advantage, allowing the integrated model to run on a general propose PC with a reasonable computation time. Additional improvement in computation can be obtained by use of a high-performance computer or a cluster of processors.

FIG. 1 is a schematic of the model in accordance with the invention. The simulation system is based on two models that are tightly coupled together. The finite element model of the left ventricle uses the LV pressure as the input and determines the LV volume at each and every time step. The LV elastance, defined by the instantaneous pressure/volume ratio, drives the analog electrical model that determines the pressures and flows at various parts of the cardiovascular system. The response of the circulatory model defines the LV pressures of the next time step, thus propagating the numerical integration forward in time.

Figure 2:
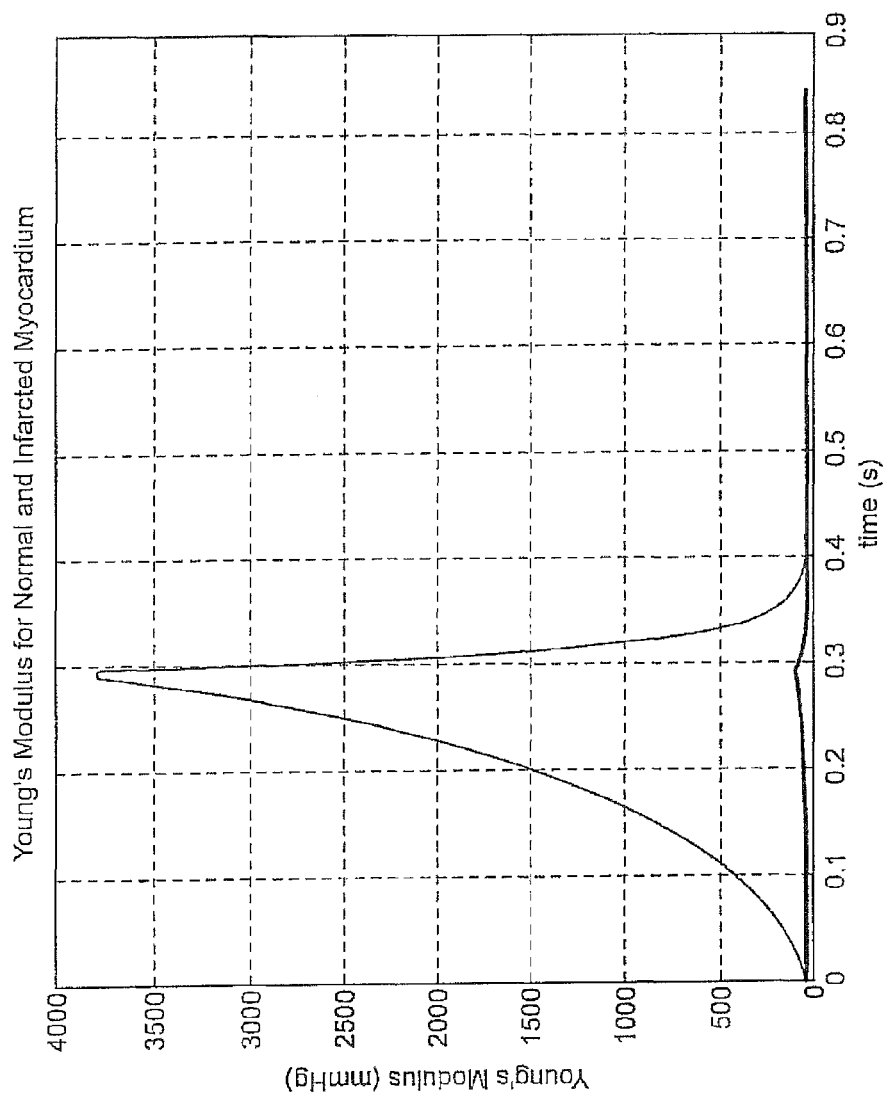
FIG. 2 is a graph of time-varying Young's modulus for normal and infarct elements.

The contraction of the finite element LV model is controlled by the time-varying Young's modulus assigned to each finite element. FIG. 2 shows the typical Young modulus curves over a cardiac cycle assigned to the normal elements (dotted) and the infarct elements (solid). The contraction of normal myocardium is associated with the increase of the Young's modulus during systole. By contrast, the infarct myocardium has a significantly reduced Young's modulus during systole.

Figure 3:
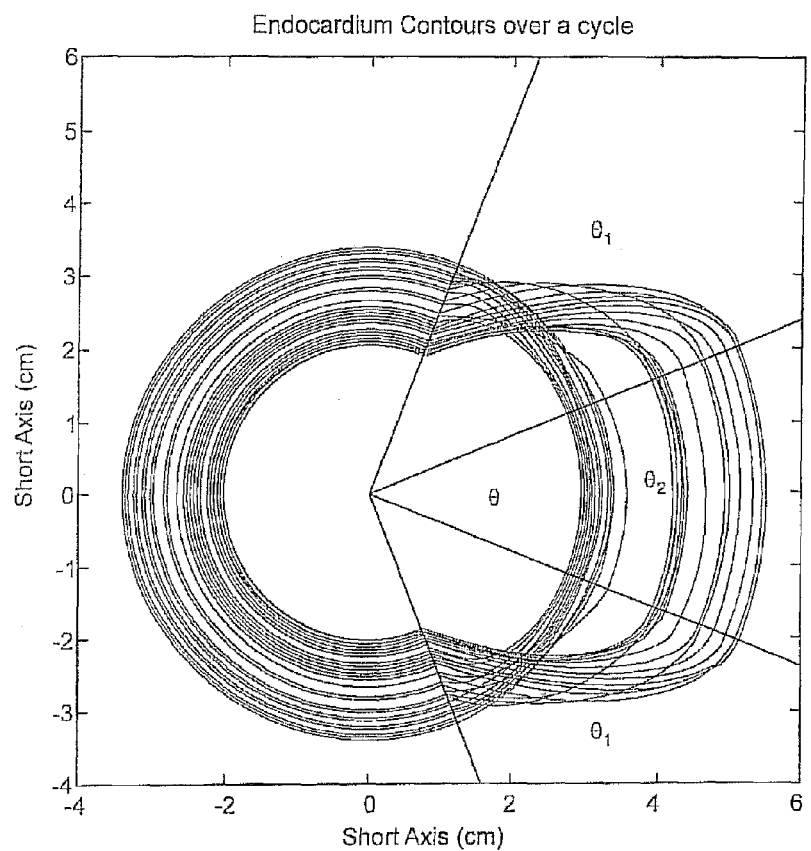
FIG. 3 is a scheme to interpolate 3D LV geometry by use of normal 2D profile and an infarct 2D profile.

Although it is possible to use a true 3D finite element LV model, the resulting computation time would be enormous. The current interest is the global LV elastance, not the details of regional wall motion. It is sufficient to use two or more 2D LV wall profiles to interpolate the 3D LV geometry. As shown by the short axis view in FIG. 3, the infarct profile is assigned to sector $\theta_2$. The two sectors $\theta_1$ are transitional from the infarct profile to the normal profile. The endocardial border of this sector is interpolated with the square root of the sinusoidal function. The normal sector is assumed to be axis symmetrical.

The tight coupling between the finite element model and the circulatory model is advantageous in a sense that the finite element LV model constantly receives feedback from the circulatory system. This feedback allows the LV model to be an integrated part of the overall cardiovascular system, thereby making it behaves in a more physiological way. For examples, the LV may contract differently under the condition of high systemic arterial resistance (hypertension) or an insufficient mitral valve (mitral regurgitation). The interaction between the finite element model and the circulatory model at each and every time step is shown below:

1. The circulatory model determines the LV pressure ($p_{lv}$).
2. The finite element model uses $p_{lv}$ as input and determines the LV volume ($v_{lv}$)
3. The LV elastance is computed according to: $e_{lv}=p_{lv}/v_{lv}$.
4. The new $e_{lv}$ is used to drive the circulatory model.
5. Go to step 1 and start the next iteration.

Figure 4:
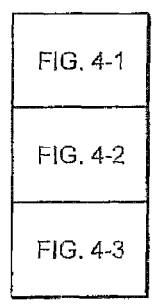
Figures 1, 4:
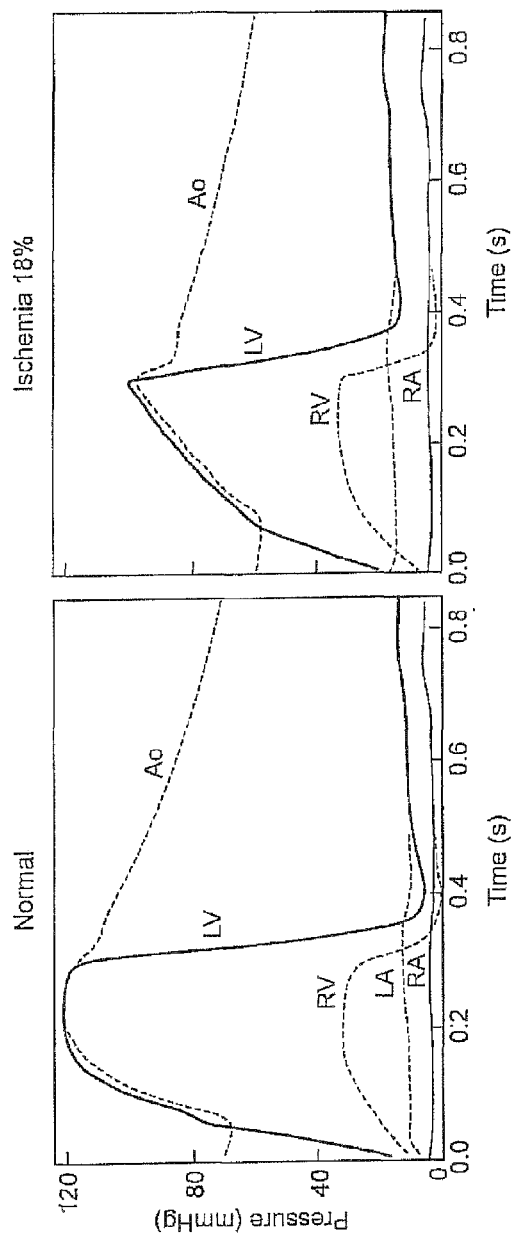
Figures 2, 4:
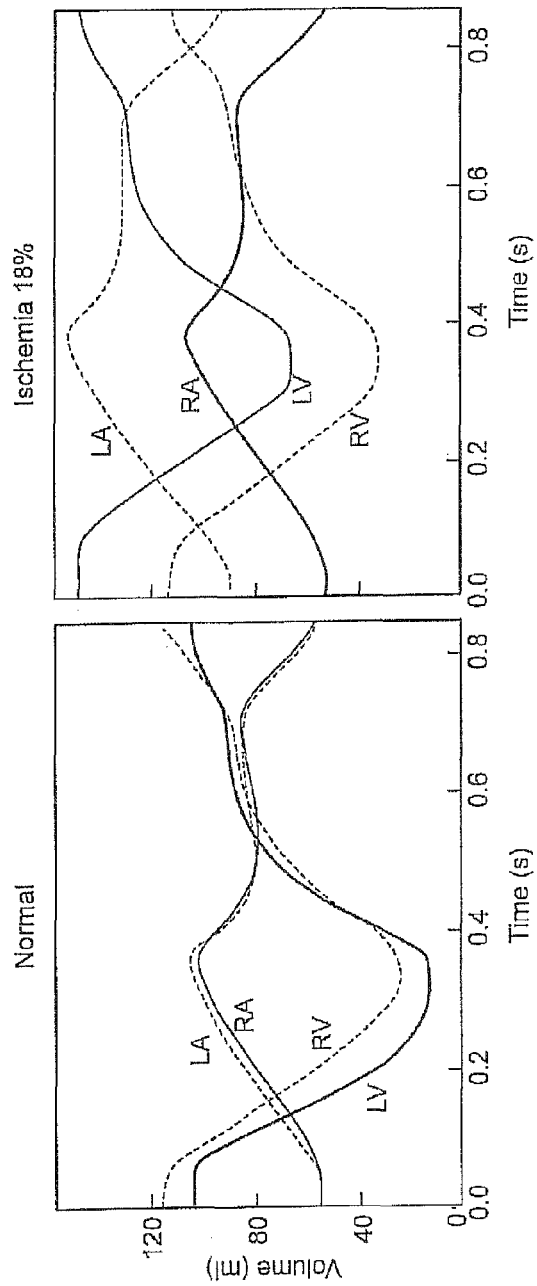
Figure 5A:
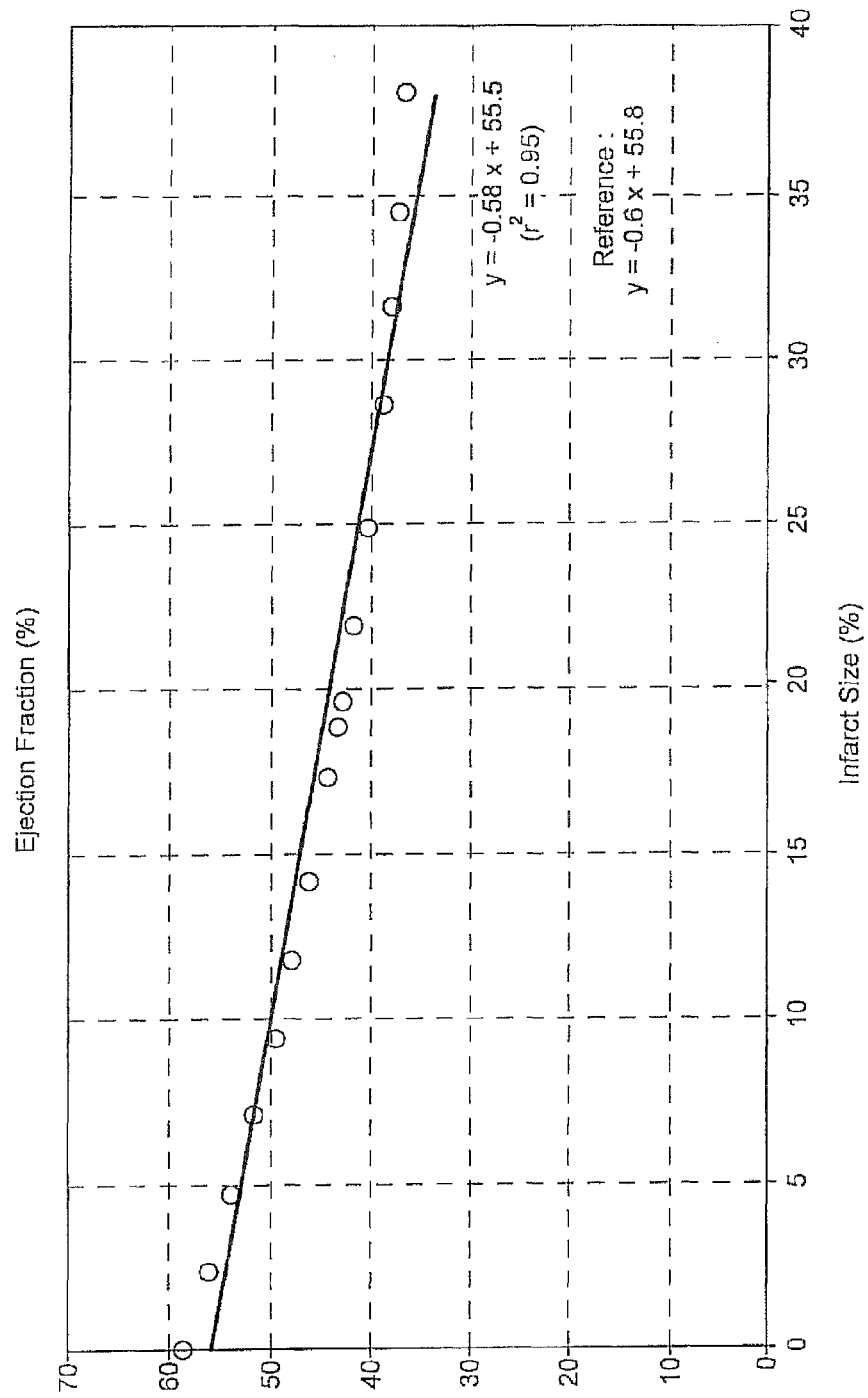
FIGS. 5 through 5B are graphs of the model results versus clinical data.
Figure 5B:
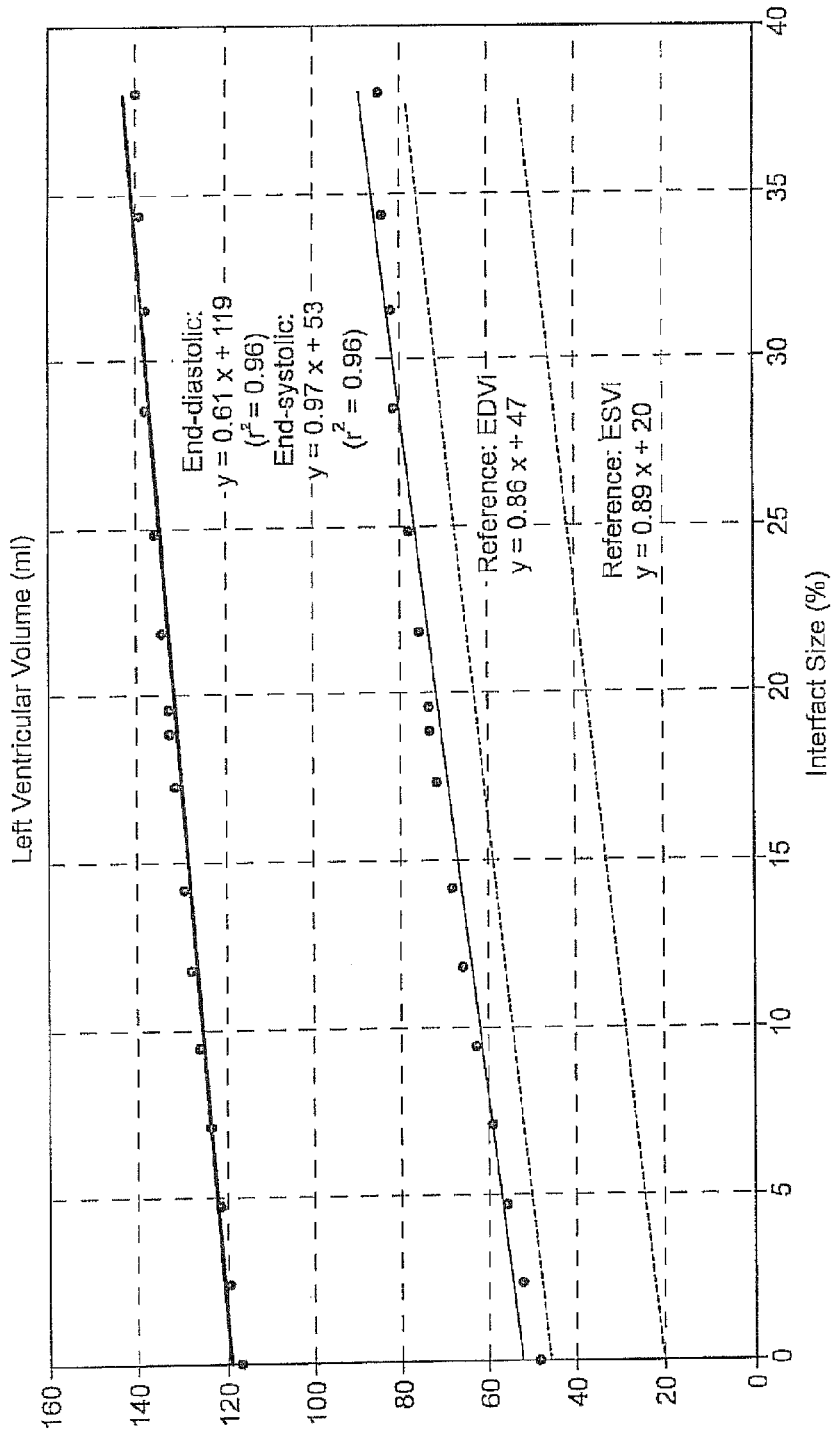

FIG. 4 shows the hemodynamic waveforms generated by the cardiovascular system for the normal case and a case of 18% LV infarction. Whereas in FIG. 5 the model predicted the effects of LV infarct size on the ejection fraction (EF) and LV end-systolic and end-diastolic volumes. The solid lines are linear regression lines fitted to the model results. The dotted lines are linear regressions lines fitting to patient data reported by Sciagra R, Imperiale A, Antoniucci D, Parodi G, Comis G, Pupi A. Relationship of infarct size and severity versus left ventricular ejection fraction and volumes obtained by 99mTc-sestamibi gated single-photon emission computed tomography in patients treated with primary percutaneous coronary intervention. European J Nuclear Medicine & Molecular Imaging 31: 969-974, 2004. In the case of the EF (top) the model result matched the clinical data almost exactly. In the case of LV volumes, the clinical data were normalized to the body surface area, which the model did not represent. Nevertheless the slopes of the regression lines matched very well. Thus, this simulation study supported the validity of the model. The model is not only capable of characterizing the contractility and preload relations but also quantitatively accurate in predicting the hemodynamic effects of varying the LV infarct size.

The model predicted the transient phase of the LV volume in response to the introduction of a 20% infarction at time=0. The model usually takes 15 to 25 cardiac cycles to reach a steady state. Currently the computation time is about 30 minutes for a cardiac cycles on a 3 GHz PC. The simulation shown here contains 18 cardiac cycles. Thus, it took 9 hours to complete. This example also demonstrates the importance of having a computation-efficient model.

The immediate applications of the integrated model are in the area of research in cardiovascular dynamics and computed-assisted instruction of cardiovascular physiology.

Future applications include the ventricular restoration surgery Cohn L H. Chen F Y, Cohn L H. The surgical treatment of heart failure. A new frontier: nontransplant surgical alternatives in heart failure. Cardiology Review 10(6): 326-33, 2002. As an alternative to heart transplant, ventricular restoration surgery removes the infract myocardium and pulls the viable muscles together. The goals of this surgery are to return the LV a more normal shape and to make LV more efficient. Certain procedures of ventricular restoration surgery have recently received FDA approvals. So far in the present recommended ventricular restoration surgery, the Dor procedure, the borders between the infarction and viable contracting myocardium is determined by visual inspection and palpation identification during the surgery. The myocardium within the borders is removed. This procedure needs a very experienced team. The model offers a method to predict the hemodynamic results of regional infarction before and after the restoration surgery, thus to assist in determining the appropriate amount of infarct myocardium to be removed.

Additionally the model can be used to predict the hemodynamic effects of action potential propagation in the myocardium. The hemodynamic waveforms in FIG. 4 were generated by the model under the assumption that all finite elements began to contract at the same time. The model is also capable of relating the various patterns of action potential propagation to their hemodynamic consequences. This can be achieved in the model by delaying the Young's modulus curve for each element according to the arrival time of the action potential wave. Such simulation will contribute to the understanding of certain clinical procedures such as cardiac resynchronization therapy (CRT). The CRT has recently been approved by the FDA as a procedure to treat congestive heart failure Adamson P B, Abraham W T. Cardiac resynchronization therapy for advanced heart failure. Current Treatment Options Cardiovascular Medicine 5(4): 301-309, 2003. The CRT uses biventricular pacing via a catheter placed near the apex of the right ventricle and another one placed near the base of the left ventricle via the great cardiac vein. The mechanism for improved LV function observed in patients are not well understood. The proposed model should be able to study the underlying mechanisms and help optimizing the instrumental parameters of the CRT device.

Figure 6:
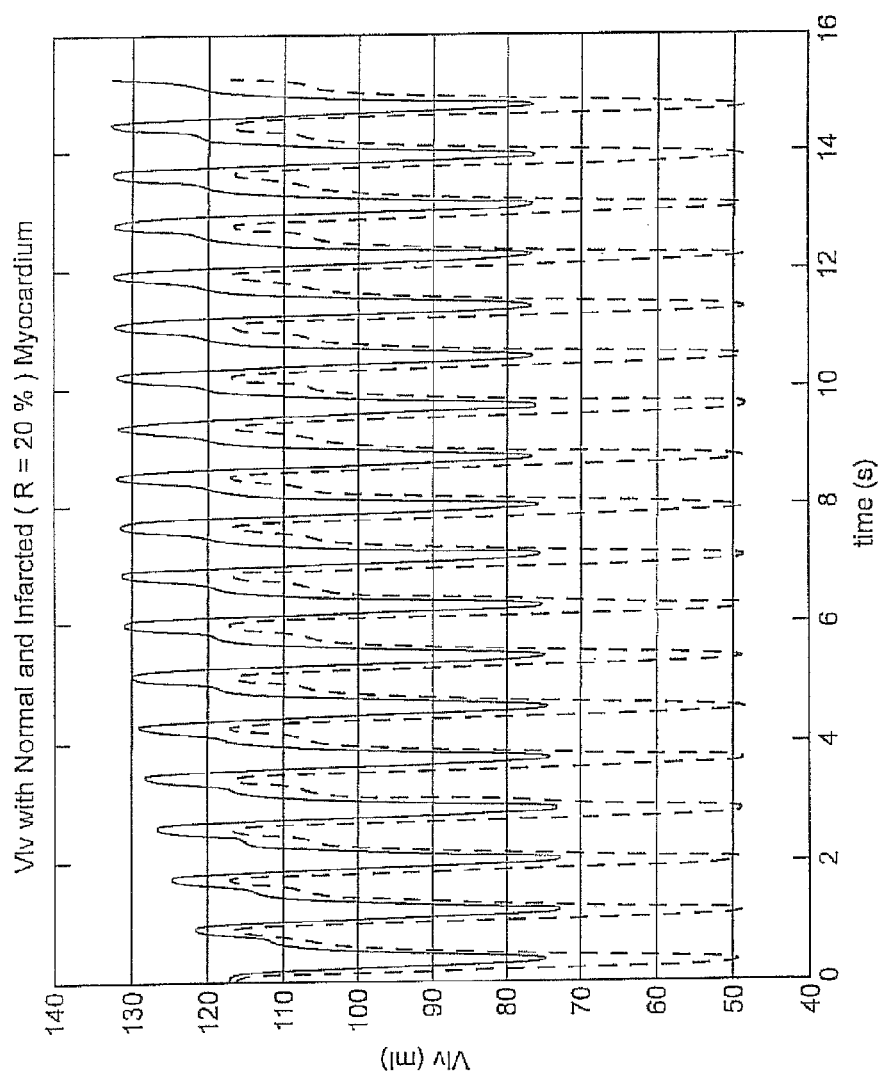
FIG. 6 is a graph demonstrating the ability of the model to represent the transient phase of the model predicted LV volume over several cardiac cycles.

This invention integrates a complex circulatory model and a finite element dynamically and efficiently. It can relate LV regional myocardial contraction to the hemodynamic consequences. The 3-dimensional geometry generated by two 2-dimensional finite element calculations significantly decreases the computation time. Traditional 3D finite element LV models usually take days to compute and require supercomputers or cluster processors. With the algorithm, it is possible to run many cardiac cycles continuously to reveal the transient phase within a relative short time (FIG. 6). The circulatory model is also much more comprehensive than the 3-element Windkessel model used in this type of models in the past. It includes the functions of four cardiac chambers, cardiac valves, pulmonary circulation, systemic arterial bed, and venous return. The model is physiological as demonstrated by the bottom panel of FIG. 5, where the preload (LV end-diastolic volume) increases in response to the infarction. No other model is capable to represent such mechanisms.

There are many advantages of the invention over the prior systems. These include the use of time-varying Young's modulus of individual finite elements to define the global LV elastance over a cardiac cycle, the definition of infarct zone by reduced Young's modulus, the use of two or more 2D LV wall profiles to interpolate the 3D LV geometry, the interaction between the finite element model and the circulatory model via the LV elastance at every integration time step, the prediction of the hemodynamic effects of action potential propagation in the myocardium, and the use of the model to assess outcomes of LV infarction, cardiac resynchronization therapy using biventricular pacing, and ventricular restoration surgery.

The model provides a platform to describe normal and abnormal left ventricles, and predicts the hemodynamic consequences of a specific infarct zone. The model has several application areas including cardiovascular research, computer assisted instruction, pharmaceutical research, planning and assessment of LV remodeling surgery, optimization of cardiac resynchronization therapy by biventricular pacing, and relating medical imaging data (MRI, SPECT, echo) to diagnosis of congestive heart failure.

The integration of the finite element LV model and the circulatory model should prove to be an important breakthrough in transitional research. This should bring the computation models out of pure research and find many applications in cardiology, cardiac surgery, medical device and pharmaceutical industry.

The model includes a more sophisticated circulatory model and the representation of normal and infarct LV geometry. The computation efficiency is another advantage, allowing the integrated model to run on a general propose PC with a reasonable computation time. Additional improvement in computation can be obtained by use of a high-performance computer or a cluster of processors.

The software system has been completely implemented in a C++ program for Windows by use of a public domain development system (wxWindow).

Although the present invention has been shown and described with respect to several preferred embodiments thereof, various changes, omissions and additions to the form and detail thereof, may be made therein, without departing from the spirit and scope of the invention.

What is claimed is:

1. A computational system to determine the dynamics of a left ventricle continuously over consecutive cardiac cycles, wherein said system comprises: a complex circulatory model integrated with a finite element model, wherein the system includes the following elements that interact between the finite element model and the complex circulatory model:
   (a) means for determining a LV pressure ($p_{lv}$) using the complex circulatory model to determine an input ($p_{lv}$) for the finite element model;
   (b) means for using the LV pressure ($p_{lv}$) as input for the finite element model and determining a LV volume ($v_{lv}$);
   (c) means for computing a LV elastance ($e_{lv}$) by dividing $p_{lv}$ by $v_{lv}$;
   (d) means for driving the complex circulatory model with the $e_{lv}$; and
   (e) means for returning to determining the LV pressure in step (a) and beginning a next iteration, wherein time steps continue at a sufficient time resolution for a desired number of entire cardiac cycles.

2. The computational system of claim 1 wherein said system is configured to assign dynamic Young's modulus functions to individual finite elements, resulting in a time-varying left ventricular elastance that drives the complex circulatory model.

3. The computational system of claim 1 wherein said system is configured to determine three-dimensional left ventricular parameters for two or more two-dimensional finite element profiles of the left ventricular walls to achieve computational efficiency.

4. The computational system of claim 1 wherein said computational system is configured to employ an analytical function that includes the square root of a sinusoidal function to interpolate laterally between a normal wall profile and an infarct wall profile.

5. The computational system of claim 1 wherein said system is configured to extend the complex circulatory model to include all major cardiovascular compartments other than left ventricle and physiological control mechanisms.

6. The computational system of claim 1 wherein said system is configured to extend the finite element model to cardiac chambers other than the left ventricle.

7. The use of the computational system of claim 1 wherein said system is configured to determine a theoretically optimal amount of infarct mass to be removed in ventricular restoration surgery by predicting the hemodynamic consequence of removing a certain amount of infarction from an impaired left ventricle.

8. The use of the computational system of claim 1 wherein said system is configured to determine hemodynamic effects of the propagation of action potentials in myocardia.

9. A method of using a complex circulatory model integrated with a finite element model in a non-transitory computer readable medium for determining the dynamics of a left ventricle continuously over consecutive cardiac cycles, wherein said the method includes the following steps that interact between the finite element model and the complex circulatory model at a set of time steps:
   (a) determining a LV pressure ($p_{lv}$) using the complex circulatory model to determine an input ($p_{lv}$) for the finite element model;
   (b) using the LV pressure ($p_{lv}$) as input for the finite element model and determining a LV volume ($v_{lv}$);
   (c) computing a LV elastance ($e_{lv}$) by dividing $p_{lv}$ by $v_{lv}$;
   (d) driving the complex circulatory model with the $e_{lv}$; and
   (e) returning to the step of determining the LV pressure, step (a), and beginning a next iteration, wherein the time steps continue at a sufficient time resolution for a desired number of entire cardiac cycles.

10. The method as claimed in claim 9, wherein said method further includes the step of assigning dynamic Young's modulus functions to individual finite elements, resulting in a time-varying ventricular elastance that drives the complex circulatory model.

11. The method as claimed in claim 9, wherein said method further includes the step of determining three-dimensional left ventricular parameters for two or more two-dimensional finite element profiles of the left ventricular walls to achieve computational efficiency.

12. The method as claimed in claim 9, wherein said method further includes the step of employing an analytical function that includes the square root of a sinusoidal function to interpolate laterally between a normal wall profile and an infarct wall profile.

13. The method as claimed in claim 9, wherein said method further includes the step of determining a theoretically optimal amount of infarct mass to be removed in ventricular restoration surgery.

14. The method as claimed in claim 13, wherein said step of determining the theoretically optimal amount of infarct mass to be removed in ventricular restoration surgery involves predicting the hemodynamic consequence of removing a certain amount of infarction from an impaired left ventricle.

15. The method as claimed in claim 9, wherein said method further includes the step of determining hemodynamic effects of the propagation of action potentials in myocardia.

16. A computational system to determine the dynamics of a left ventricle continuously in a cardiovascular system over consecutive cardiac cycles, wherein said system comprises: a complex circulatory model integrated with a finite element model, wherein the system includes the following elements that interact between the finite element model and the complex circulatory model:
   (a) means for determining a LV pressure ($p_{lv}$) using the complex circulatory model to determine an input ($p_{lv}$) for the finite element model;
   (b) means for using the LV pressure ($p_{lv}$) as input for the finite element model and determining a LV volume ($v_{lv}$);
   (c) means for computing a LV elastance ($e_{lv}$) by dividing $p_{lv}$ by $v_{lv}$;
   (d) means for driving the complex circulatory model with the $e_{lv}$, to determine pressures and flows at a plurality of parts of the cardiovascular system; and
   (e) iterative means for again:
      determining the LV pressure ($p_{lv}$) using the complex circulatory model to determine an input ($p_{lv}$) for the finite element model;
      using the LV pressure ($p_{lv}$) as input for the finite element model and determining the LV volume ($v_{lv}$);
      computing the LV elastance ($e_{lv}$) by dividing $p_{lv}$ by $v_{lv}$; and
      driving the complex circulatory model with the $e_{lv}$, to determine pressures and flows at the plurality of parts of the cardiovascular system,
   until a desired number of entire cardiac cycles are performed.

17. The computational system of claim 16 wherein said computational system is configured to employ an analytical function that includes the square root of a sinusoidal function to interpolate laterally between a normal wall profile and an infarct wall profile.

18. The computational system of claim 16 wherein said system is configured to assign dynamic Young's modulus functions to individual finite elements.

19. The use of the computational system of claim 16 wherein said system is configured to determine a theoretically optimal amount of infarct mass to be removed in ventricular restoration surgery by predicting the hemodynamic consequence of removing a certain amount of infarction from an impaired left ventricle.

20. The use of the computational system of claim 16 to determine hemodynamic effects of the propagation of action potentials in myocardia.

* * * * *